United States Patent
Heston

(10) Patent No.: US 10,177,700 B2
(45) Date of Patent: Jan. 8, 2019

(54) SURGICAL POWER TOOL WITH CRITICAL ERROR HANDLER

(71) Applicant: Zimmer, Inc., Warsaw, IN (US)

(72) Inventor: Brian Keith Heston, Bolivar, OH (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/784,571

(22) Filed: Oct. 16, 2017

(65) Prior Publication Data

US 2018/0123500 A1    May 3, 2018

Related U.S. Application Data

(60) Provisional application No. 62/414,995, filed on Oct. 31, 2016.

(51) Int. Cl.
| | |
|---|---|
| *H02P 1/00* | (2006.01) |
| *H02P 29/024* | (2016.01) |

(Continued)

(52) U.S. Cl.
CPC .......... *H02P 29/0241* (2016.02); *A61B 17/00* (2013.01); *A61B 17/1626* (2013.01); *G05B 15/02* (2013.01); *H02K 7/145* (2013.01); *H02P 29/60* (2016.02); *A61B 17/32002* (2013.01); *A61B 2017/00017* (2013.01); *A61B 2017/00084* (2013.01); *A61B 2017/00123* (2013.01); *A61B 2017/00221* (2013.01); *A61B 2017/00398* (2013.01); *G06F 19/3481* (2013.01)

(58) Field of Classification Search
CPC ..... H02J 7/0021; H02P 29/0241; H02K 7/145
See application file for complete search history.

(56) References Cited

U.S. PATENT DOCUMENTS

| | | |
|---|---|---|
| 5,888,200 A | 3/1999 | Walen |
| 5,941,891 A | 8/1999 | Walen |

(Continued)

FOREIGN PATENT DOCUMENTS

WO    2018080823    5/2018

OTHER PUBLICATIONS

"International Application Serial No. PCT/US2017/056740, International Search Report dated Feb. 16, 2018", 4 pgs.

(Continued)

*Primary Examiner* — Karen Masih
(74) *Attorney, Agent, or Firm* — Schwegman Lundberg & Woessner, P.A.

(57) ABSTRACT

In a surgical power tool that includes an electric motor positioned in a housing and a movable element extending from the housing and operatively actuated by the electric motor, a controller can repeatedly interrogate for faults a plurality of components in or on the housing, such as the electric motor, the controller, a battery, a trigger, and a mode switch. Upon finding a component in a fault condition, the controller can engage a critical error handler that disengages the electric motor, disables at least some of the plurality of components, and directs a microprocessor in the controller into a safe software state. Upon engaging the critical error handler, the controller can further write to a memory an error code corresponding to which of the plurality of components is in the fault condition. The error code can be accessible via a wired or wireless connection.

20 Claims, 8 Drawing Sheets

(51) Int. Cl.
  *H02P 29/60* (2016.01)
  *A61B 17/00* (2006.01)
  *G05B 15/02* (2006.01)
  *H02K 7/14* (2006.01)
  *A61B 17/16* (2006.01)
  *G06F 19/00* (2018.01)
  *A61B 17/32* (2006.01)

(56) References Cited

U.S. PATENT DOCUMENTS

| | | | |
|---|---|---|---|
| 6,017,354 | A | 1/2000 | Culp et al. |
| 6,025,683 | A | 2/2000 | Philip |
| 6,099,494 | A | 8/2000 | Henniges et al. |
| 6,220,368 | B1 | 4/2001 | Ark et al. |
| 6,329,778 | B1 | 12/2001 | Culp et al. |
| 6,500,169 | B1 | 12/2002 | Deng |
| 6,752,816 | B2 | 6/2004 | Culp et al. |
| 6,786,897 | B2 | 9/2004 | McIe et al. |
| 6,958,071 | B2 | 10/2005 | Carusillo et al. |
| 6,960,894 | B2 | 11/2005 | Carusillo et al. |
| 7,422,582 | B2 | 9/2008 | Malckowski et al. |
| 7,517,351 | B2 | 4/2009 | Culp et al. |
| 7,638,958 | B2 | 12/2009 | Philipp et al. |
| 7,998,157 | B2 | 8/2011 | Culp et al. |
| 8,029,510 | B2 | 10/2011 | Hoegerle |
| 8,115,126 | B2 | 2/2012 | Deng et al. |
| 8,157,827 | B2 | 4/2012 | Murphy et al. |
| 8,241,235 | B2 | 8/2012 | Kahler et al. |
| 8,493,009 | B2 | 7/2013 | Hafner et al. |
| 8,523,845 | B2 | 9/2013 | Ippisch |
| 8,734,449 | B2 | 5/2014 | Schmied et al. |
| 8,784,415 | B2 | 7/2014 | Malackowski et al. |
| 8,790,331 | B2 | 7/2014 | Stanton |
| 8,870,861 | B2 | 10/2014 | El-Galley et al. |
| 2005/0217874 | A1* | 10/2005 | Forster ............... B25C 1/06 173/1 |
| 2010/0289497 | A1* | 11/2010 | Lum-Shue-Chan ................ G01R 31/3658 324/426 |
| 2013/0245704 | A1 | 9/2013 | Koltz et al. |
| 2015/0182230 | A1* | 7/2015 | Belagali ............... A61B 17/14 606/82 |
| 2015/0201918 | A1 | 7/2015 | Kumar et al. |
| 2016/0350519 | A1* | 12/2016 | Pattyn ............... G06F 21/10 |

OTHER PUBLICATIONS

"International Application Serial No. PCT/US2017/056740, Written Opinion dated Feb. 16, 2018", 8 pgs.

* cited by examiner

SURGICAL POWER TOOL WITH CRITICAL ERROR HANDLER

CLAIM OF PRIORITY

This application claims the benefit of U.S. Provisional Patent Application Ser. No. 62/414,995, filed on Oct. 31, 2016, the benefit of priority of which is claimed hereby, and which is incorporated by reference herein in its entirety.

FIELD OF THE DISCLOSURE

The present disclosure relates to monitoring and checking for component errors in a surgical power tool.

BACKGROUND OF THE DISCLOSURE

A surgical power tool, such as a variable speed drill, can interact with human bone and tissue. It is important that the surgical power tool avoid unintended contact or damage to the bone and tissue as much as possible.

SUMMARY

In one embodiment of a surgical power tool, an electric motor can be positioned in a housing. A movable element can extend from the housing and be operatively actuated by the electric motor. A controller can be positioned in the housing and configured to: repeatedly interrogate a plurality of components in or on the housing to determine if any of the plurality of components are in a fault condition, the plurality of components including the electric motor. When at least one of the plurality of components is in a fault condition, the controller can engage a critical error handler that: disengages the electric motor, disables at least some of the plurality of components, and directs a microprocessor in the controller into a safe software state.

In another embodiment, in a method for monitoring the operation of a surgical power tool, the surgical power tool can include a plurality of components positioned in or on a housing. With the controller, the method can periodically interrogate the plurality of components to determine if any of the plurality of components are in a fault condition. When at least one of the plurality of components is in a fault condition, the controller can engage a critical error handler that: disengages an electric motor, disables at least some of the plurality of components, and directs a microprocessor in the controller into a safe software state.

In another embodiment, a surgical power tool can include a housing. An electric motor can be positioned in the housing. A movable element can extend from the housing and be operatively actuated by the electric motor. A controller can be positioned in the housing. A battery can supply electrical power to the controller. A trigger can be coupled to the controller and can turn on the electric motor when the trigger is depressed and adjust a speed of the electric motor based on how far the trigger is depressed. A mode switch can be coupled to the controller and can select among at least two specified modes of operation for the controller. The electric motor, the controller, the battery, the trigger, and the mode switch can form a plurality of components. The controller can: repeatedly interrogate the plurality of components to determine if any of the plurality of components are in a fault condition; and when at least one of the plurality of components is in a fault condition, engage a critical error handler that: disengages the electric motor, disables the trigger and the mode switch, directs a microprocessor in the controller into a safe software state, and causes a sound emitter to emit an audible alarm.

BRIEF DESCRIPTION OF THE DRAWINGS

Corresponding reference characters indicate corresponding parts throughout the several views. Elements in the drawings are not necessarily drawn to scale. The configurations shown in the drawings are merely examples, and should not be construed as limiting the scope of the invention in any manner.

DETAILED DESCRIPTION

In a surgical power tool that includes an electric motor positioned in a housing and a movable element extending from the housing and operatively actuated by the electric motor, a controller can repeatedly interrogate for faults a plurality of components in or on the housing, such as the electric motor, the controller, a battery, a trigger, and a mode switch. Upon finding a component in a fault condition, the controller can engage a critical error handler that disengages the electric motor, disables at least some of the plurality of components, and directs a microprocessor in the controller into a safe software state. Upon engaging the critical error handler, the controller can further write to a memory an error code corresponding to which of the plurality of components is in the fault condition. The error code can be accessible via a wired or wireless connection.

Using a critical error handler in this manner can quickly address problems in the surgical power tool, which can reduce the risk of damaging bone and tissue during use or damaging the surgical power tool. Once the critical error handler has been engaged, the surgical power tool can be powered down and then powered up and/or reset to resume operation. If the surgical power tool engages the critical error handler more than once, the surgical power tool could need servicing outside the surgical arena.

Figure 1:
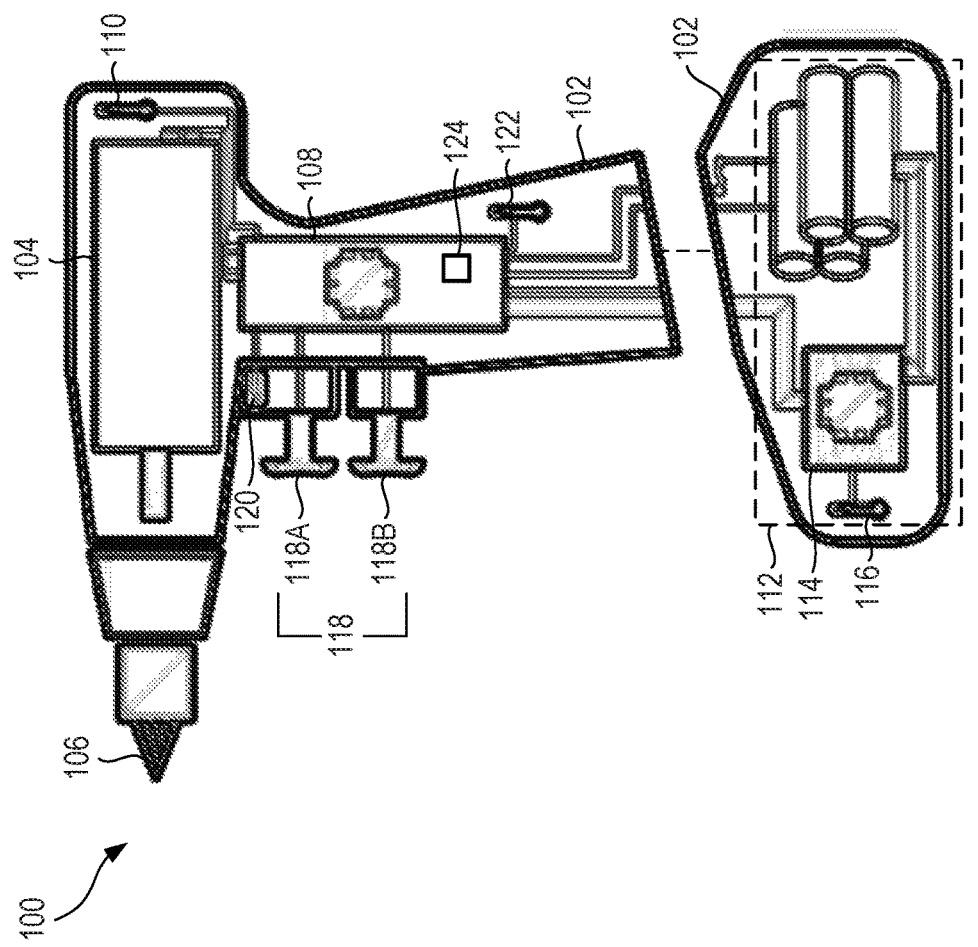
FIG. 1 shows an example of a surgical power tool, in accordance with some embodiments.

FIG. 1 shows an example of a surgical power tool 100, in accordance with some embodiments. In the example of FIG. 1, the surgical power tool 100 of FIG. 1 is configured as a power drill. It will be understood that a power drill is but one example of a surgical power tool; other suitable configurations can also be used, such as a saw, a reamer, a boneshaper, and others.

The surgical power tool 100 can include a housing 102. In the example of FIG. 1, the housing 102 is shaped such that a surgeon can grip the housing with one hand. The housing 102, and its contents, can be sterilized suitably, so that the surgical power tool 100 can operate in a sterile surgical environment.

An electric motor 104 can be positioned in the housing 102. In some examples, the electric motor 104 can run at a variable, selectable speed.

A movable element 106 can extend from the housing 102 and can be operatively actuated by the electric motor 104. In the example of FIG. 1, in which the surgical power tool is configured as a power drill, the movable element 106 is a coupling that can accept a drill bit or a screw bit. In the example of FIG. 1, the movable element 106 is coupled by a shaft to the electric motor 104, so that as the electric motor 104 rotates about a longitudinal axis coincident with the movable element 106, the movable element 106 also rotates about the longitudinal axis. In other examples, the surgical power tool 100 can optionally include additional mechanical couplings to convert the rotation of the electric motor 104 into suitable movement for the movable element 106. For instance, in examples in which the surgical power tool 100 is a reciprocating saw, the movable element 106 is a blade, and the surgical power tool 100 can include a suitable gear mechanism to convert the rotation of the electric motor 104 into a longitudinal oscillatory motion for the movable element 106. Other suitable configurations can also be used.

A controller 108 can be positioned in the housing 102. The controller 108 can include one or more microprocessors 210 (FIG. 2), along with communication circuitry that can connect the microprocessor 210 to an external device, and power management circuitry that can direct power to the electric motor 104 as needed.

In some examples, the controller 108 can repeatedly interrogate a plurality of components in or on the housing 102 to determine if any of the plurality of components are in a fault condition. The plurality of components can include the electric motor 104 and additional components discussed below. When at least one of the plurality of components is in a fault condition, the controller 108 can engage a critical error handler that disengages the electric motor 104, disables at least some of the plurality of components, and directs a microprocessor in the controller 108 into a safe software state, such as an infinite loop that requires user intervention to proceed.

A machine-readable storage medium or other storage device can include any non-transitory mechanism for storing information in a form readable by a machine (e.g., a computer). In the case of program code executing on programmable computers, the computing device can include a processor on the controller 108, a storage medium readable by the processor (including volatile and non-volatile memory and/or storage elements), at least one input device, and at least one output device. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

Figure 2:
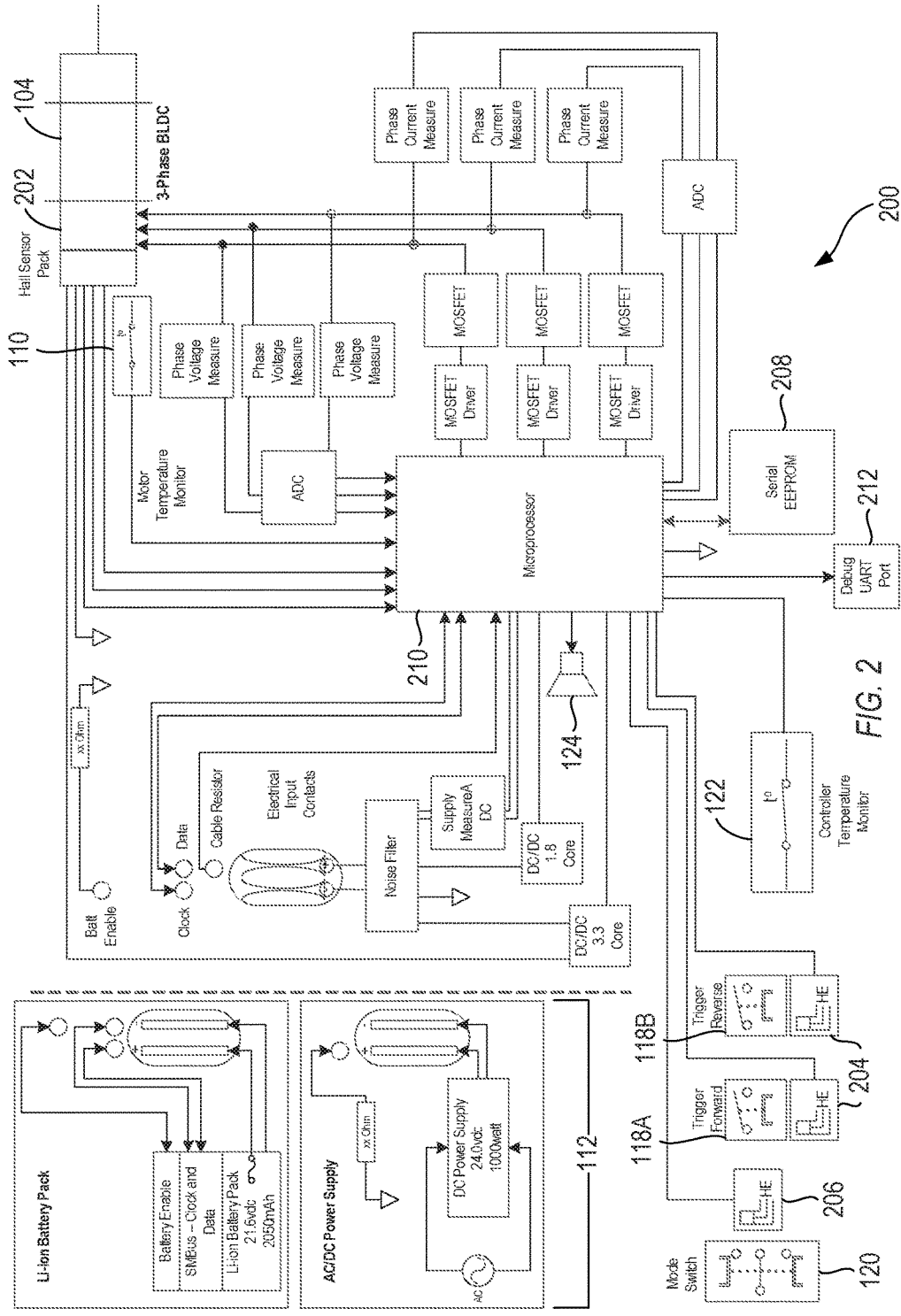
FIG. 2 shows an example of a hardware block diagram suitable for use in the surgical power tool of FIG. 1, in accordance with some embodiments.

The controller 108 can include a serial electrically erasable programmable read-only memory (EEPROM) 208 (FIG. 2). The microprocessor can read from and write to the EEPROM 208. The microprocessor can store measured values of particular parameters on the EEPROM 208, and can lookup stored values of particular parameters from the EEPROM 208. The critical error handler can be implemented as instructions in software that are stored in memory and/or on a machine-readable medium. Some or all of the instructions can be hard-wired into circuitry in the controller 108.

In some examples, the controller 108 can repeatedly interrogate the electric motor 104 for at least one of voltage, current, temperature, and phase elements.

In some examples, the plurality of components can include a motor temperature sensor 110 that can measure a temperature of the electric motor 104. The controller 108 can determine that the electric motor 104 is in the fault condition, or nearing a fault condition, when the measured temperature of the electric motor 104 exceeds a stored motor temperature value.

In some examples, the plurality of components can include a plurality of motor Hall effect sensors 202 (FIG. 2) that can determine a phase of the electric motor 104 and can generate a signal representing a speed of the electric motor 104 when the electric motor is operational 104. The controller can determine that the plurality of motor Hall effect sensors 202 are in the fault condition when at least one of the plurality of motor Hall effect sensors 202 produces a voltage outside a specified motor Hall effect sensor voltage range.

In some examples, the plurality of components can include a battery 112 that can supply electrical power to the controller 108, and to the electric motor 104 via the controller 108. In some examples, the battery 112 can be formed from one or more battery cells, which can optionally be rechargeable. The controller can repeatedly interrogate the battery 112 for at least one of a system voltage, a battery pack status flag, and a temperature. The controller can determine that the battery 112 is in the fault condition when at least one of the system voltage, battery pack status flag, or temperature exceeds a respective stored value. In some examples, the battery can include additional circuitry 114 and a battery temperature sensor 116.

In some examples, the plurality of components can include a trigger 118 coupled to the controller 108. The trigger 118 can turn on the electric motor 104 when the trigger 118 is depressed and adjust a speed of the electric motor 104 based on how far the trigger 118 is depressed. In some examples, the trigger 118 can include one or more buttons 118A, 118B that can be depressed by a surgeon when the surgeon is holding the housing 102 with one hand. In some examples, the trigger 118 can include a first button that rotates the electric motor 104 in a first direction, and a second button that rotates the electric motor 104 in a second direction, opposite the first direction.

The plurality of components can include a plurality of trigger Hall effect sensors 204 (FIG. 2) that can generate a signal representing a position of the trigger 118. The controller 108 can determine that the plurality of trigger Hall effect sensors 204 are in the fault condition when at least one of the plurality of trigger Hall effect sensors produces a voltage outside a specified trigger Hall effect sensor voltage range. The controller 108 can disable the trigger 118 (e.g., and ignore an output from the trigger) when at least one of the plurality of components is in a fault condition.

The plurality of components can include a mode switch 120 coupled to the controller 108. The mode switch 120 can select among at least two specified modes of operation for the controller, such as ON and STANDBY, or CALIBRATION and DEBUG. Other suitable modes can also be used, and other suitable numbers of modes can also be used.

The plurality of components can include a plurality of mode Hall effect sensors 206 (FIG. 2) that can generate a signal representing a position of the mode switch 120. The controller 108 can determine that the plurality of mode Hall effect sensors 206 are in the fault condition when at least one of the plurality of mode Hall effect sensors produces a voltage outside a specified mode Hall effect sensor voltage range. The controller 108 can disable the mode switch 120 (e.g., and ignore an output from the mode switch) when at least one of the plurality of components is in a fault condition.

The plurality of components can include a controller temperature sensor 122 that can measure a temperature of the controller 108. The controller 108 can determine that the controller 108 is in the fault condition, or is nearing a fault condition, when the measured temperature of the controller 108 exceeds a stored controller temperature value.

In some examples, a sound emitter 124 can be coupled to the controller 108. In some examples, the critical error handler causes the sound emitter 124 to emit an audible alarm.

In the example of FIG. 1, the housing 102 is formed as two attachable and detachable elements, with the battery 112 in one portion and the remainder of the components in the other portion. The two portions can be in wired and/or wireless communication with each other, and, optionally in wired and/or wireless communication with an external device, such as a stand-alone or network-connected computer. In other examples, the housing 102 can be formed as an integral unit, or formed with more than two elements.

FIG. 2 shows an example of a hardware block diagram suitable for use in the surgical power tool 100 of FIG. 1, in accordance with some embodiments. The circuitry 200 of FIG. 2 is but one example; other suitable circuitry can also be used.

Figure 3:
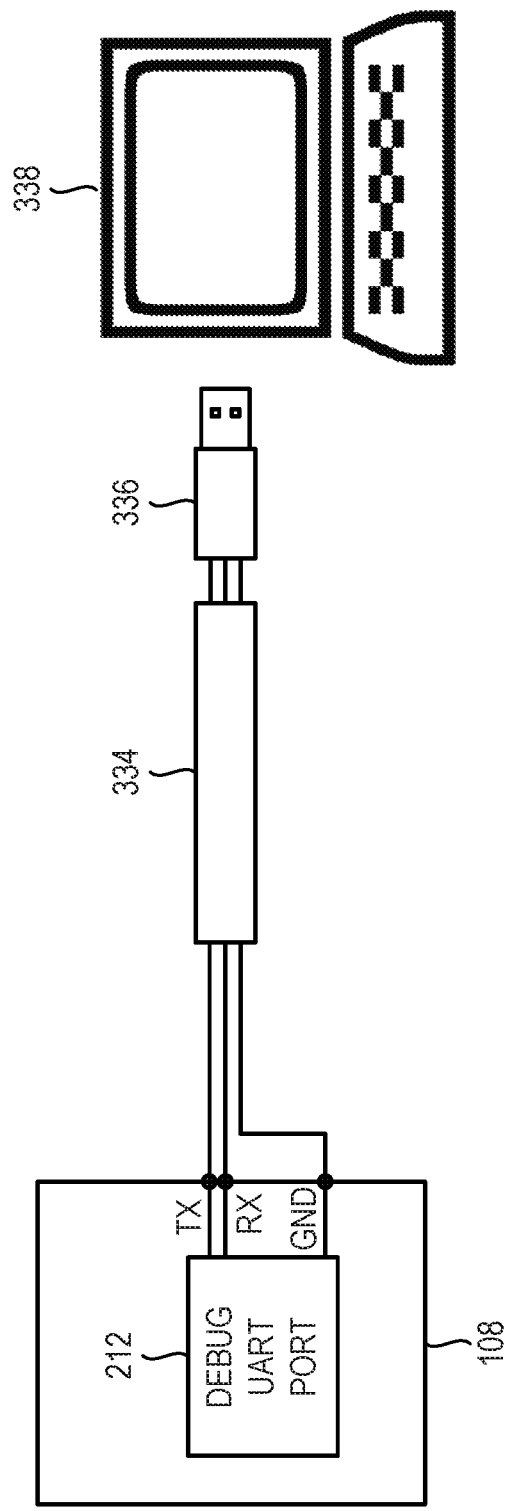
FIG. 3 shows an example of connectivity between a controller of a surgical power tool and a computer, in accordance with some embodiments.

FIG. 3 shows an example of connectivity between a controller 308 of a surgical power tool and a computer 338, in accordance with some embodiments. The connectivity shown in FIG. 3 is but one example; other suitable connectivity can also be used.

In a processor in the controller 308 of FIG. 3, a debug universal asynchronous receiver/transmitter (UART) port 212 connects to a transmission line (TX), a reception line (RX), and a ground line (GND). These three lines connect via a TTL-to-USB converter cable 334 to a USB connector 336. The USB connector 336 can removably connect to a stand-alone or network-connected computer 338. The configuration of FIG. 3 is but one example; other suitable connection types and cables can also be used.

Figure 4:
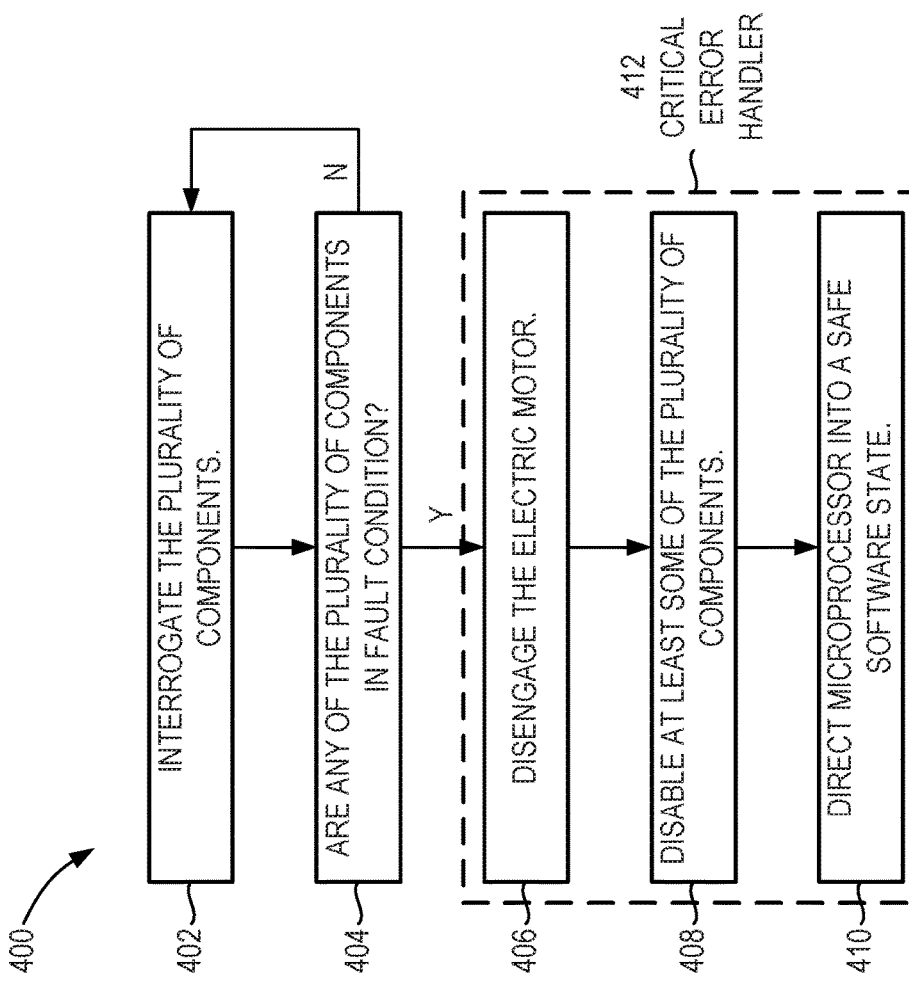
FIG. 4 shows a flowchart of an example of a method for monitoring the operation of a surgical power tool, in accordance with some embodiments.

FIG. 4 shows a flowchart of an example of a method 400 for monitoring the operation of a surgical power tool, in accordance with some embodiments. The surgical power tool can include a plurality of components positioned in or on a housing. The method 400 of FIG. 4 can be executed on a suitable surgical power tool, including surgical power tool 100 (FIG. 1) and others. Specifically, the method 400 of FIG. 4 can be executed on a controller positioned in the housing, such as controller 108 (FIG. 1) and others. The method 400 is but one method for monitoring the operation of a surgical power tool; other suitable methods can also be used.

Figure 8:
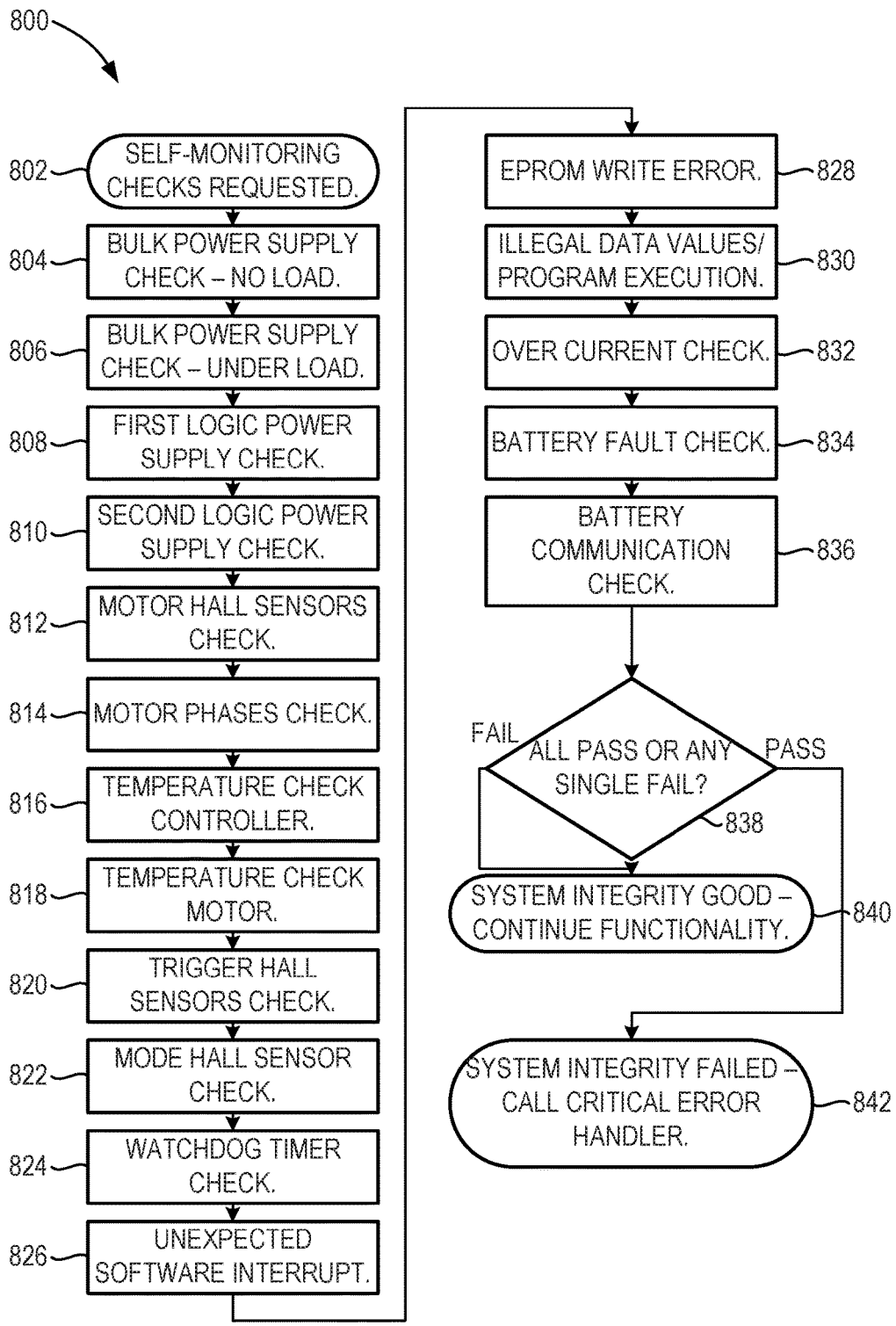
FIG. 8 shows a flowchart of an example of a method for executing a self-monitoring check for a surgical power tool, in accordance with some embodiments.

At operation 402, the controller can periodically interrogate the plurality of components to determine if any of the plurality of components are in a fault condition or nearing a fault condition. FIG. 8 (discussed below) provides a detailed example of operation 402.

At operation 404, the controller can determine if any (e.g., at least one) of the plurality of components is in a fault condition or nearing a fault condition. If, at operation 404, the controller determines that none of the plurality of components are in a fault condition or nearing a fault condition, method 400 returns to operation 402 after a suitable delay (e.g., time between interrogations). If, at operation 404, the controller determines that at least one of the plurality of components is in a fault condition, method 400 can engage a critical error handler 412.

At operation 406, the critical error handler can disengage the electric motor, such as electric motor 104 (FIG. 1).

At operation 408, the critical error handler can disable at least some of the plurality of components. In some examples, the critical error handler can disable the trigger 118 (FIG. 1) and the mode switch 120 (FIG. 1).

Figure 6:
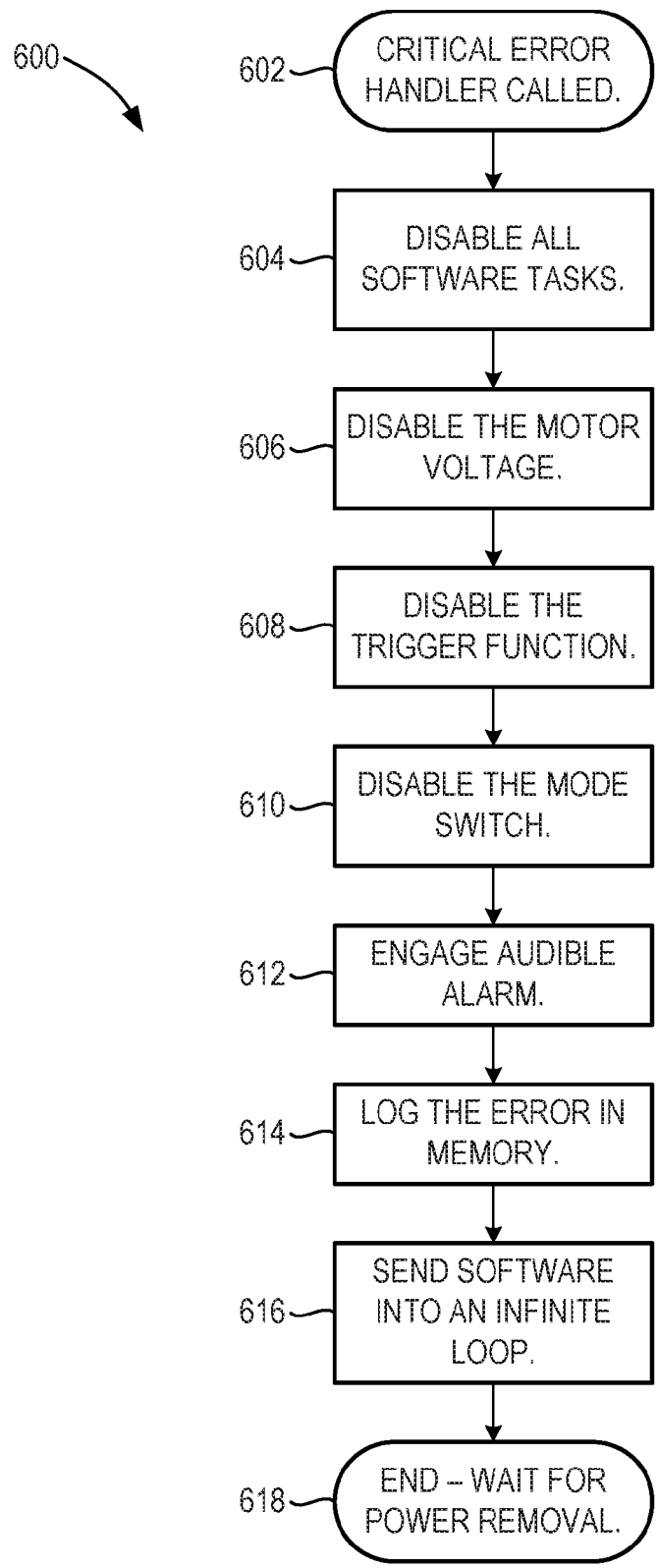
FIG. 6 shows a flowchart of an example of a method for executing a critical error handler for a surgical power tool, in accordance with some embodiments.

At operation 410, the critical error handler can direct a microprocessor, such as microprocessor 210 (FIG. 1) in the controller, such as controller 108 (FIG. 1) into a safe software state, such as an infinite loop that requires user intervention to proceed. FIG. 6 (discussed below) provides a detailed example of a critical error handler 412, which can include operations 406, 408, and 410 among others.

In some examples, method 400 can optionally further include writing to a serial electrically erasable programmable read-only memory an error code corresponding to which of the plurality of components is in the fault condition, where the error code can be accessible via a wired or wireless connection.

Figure 7:
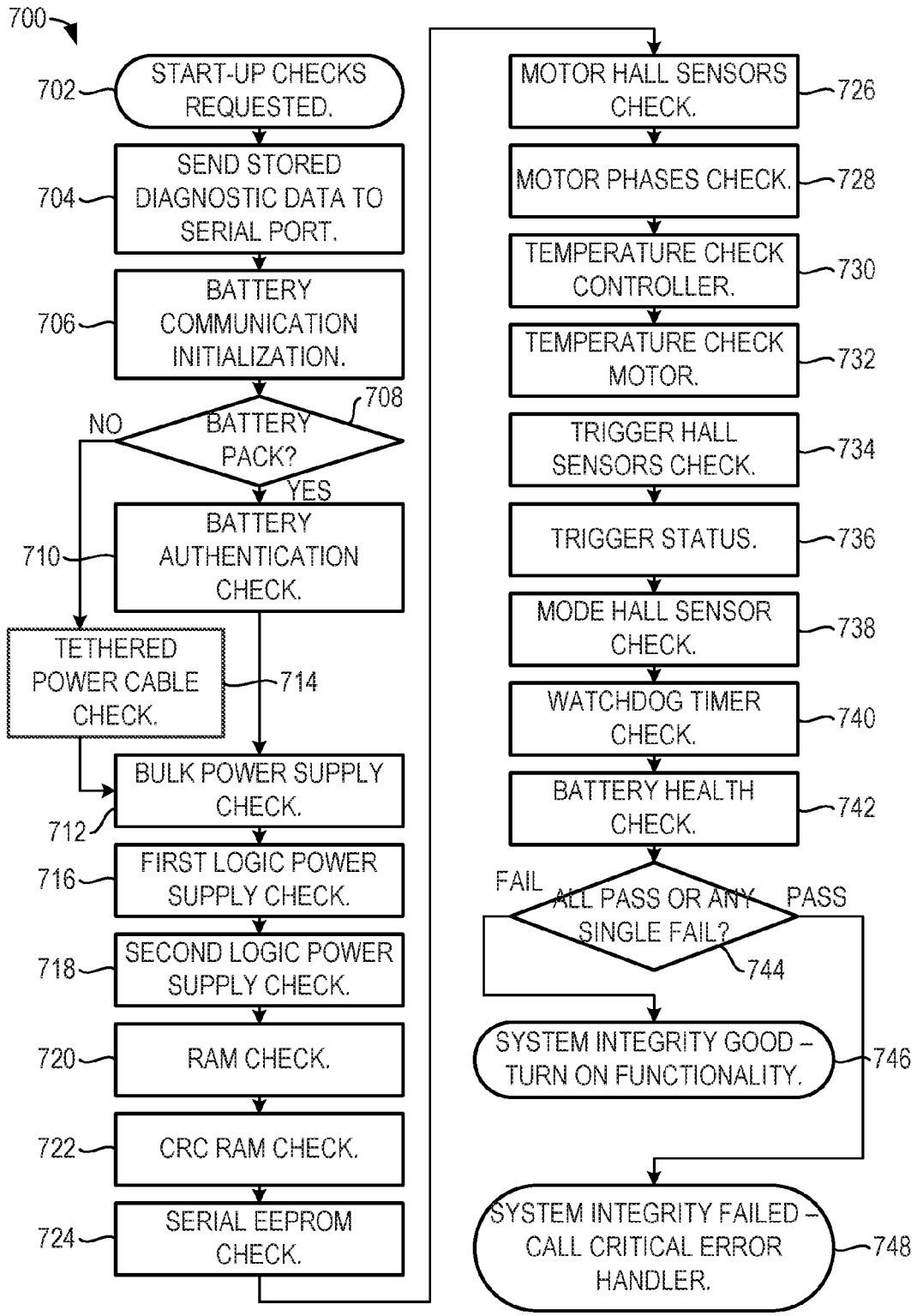
FIG. 7 shows a flowchart of an example of a method for executing a start-up integrity check for a surgical power tool, in accordance with some embodiments.

FIGS. 5-8 and the text that follows describe examples of various procedures performed by the controller when the surgical power tool is first powered up (FIG. 5), and during subsequent usage of the surgical power tool (FIGS. 6-8).

Figure 5:
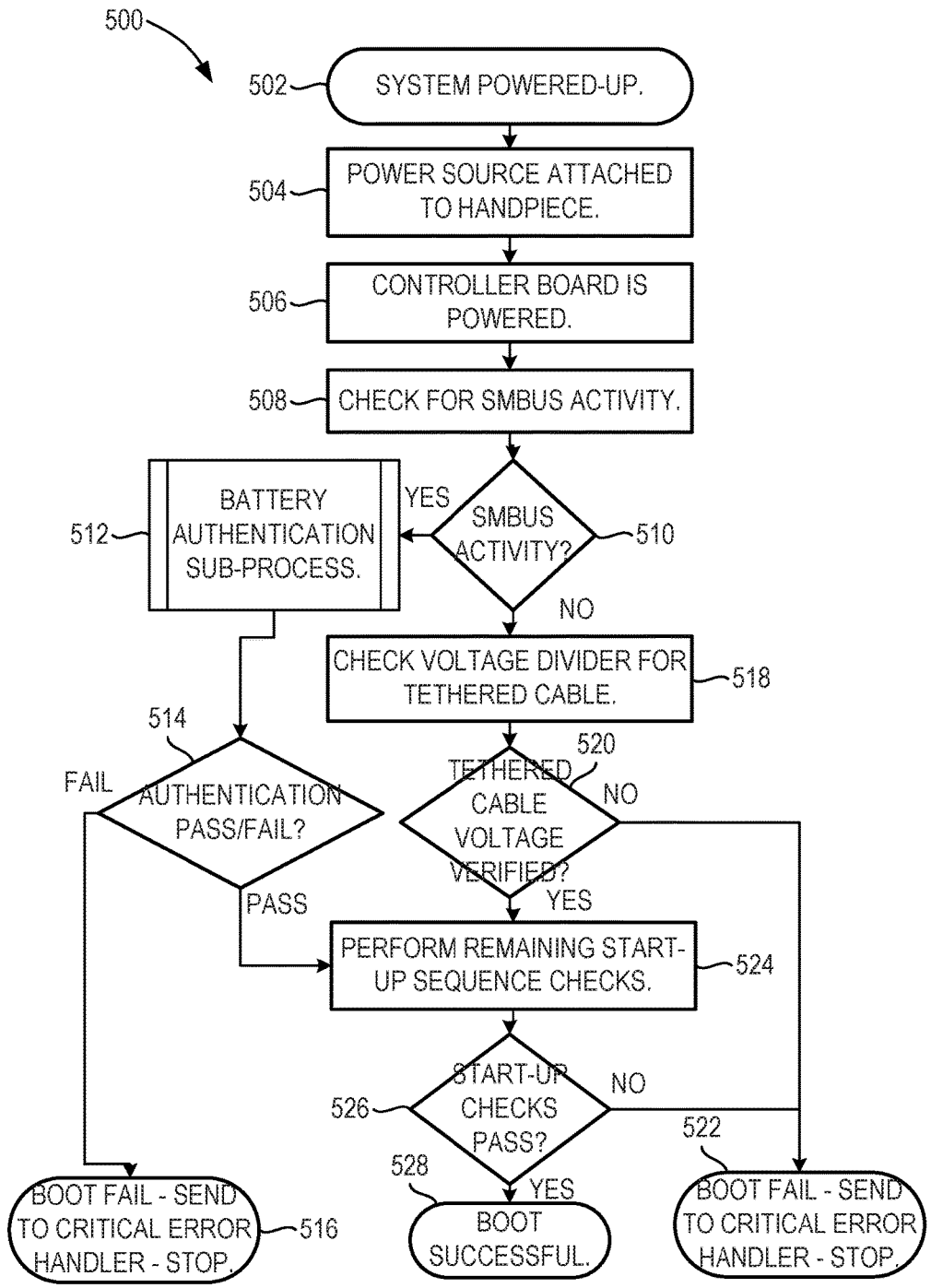
FIG. 5 shows a flowchart of an example of a method for starting up a controller for a surgical power tool, in accordance with some embodiments.

FIG. 5 shows a flowchart of an example of a method 500 for starting up a controller, such as controller 108 (FIG. 1), for a surgical power tool, such as surgical power tool 100 (FIG. 1), in accordance with some embodiments. Method 500 is but one method for starting up a controller; other suitable methods can also be used.

At operation 502, a user can power on the power surgical tool.

At operation 504, a user can connect a handpiece, such as housing 102 (FIG. 1), to a tethered AC power source that converts wall power alternating current (AC) to direct current (DC) or connect to a battery pack that is already DC. In some examples, the battery pack can include a lithium ion chemistry, although other suitable chemistries can be used.

At operation 506, a microprocessor, such as a processor in the controller 108 (FIG. 1), can begin to execute the software code.

At operation 508, the microprocessor can check for activity on a system management bus (SMBus). The SMBus can connect the microprocessor via a tethered cable to a power source for on/off instructions.

If there is activity of the SMBus, at operation 510, then at operation 512, the microprocessor checks to ensure that the power source is authentic. If, at operation 514, the power source fails to be authenticated, then the software can direct the microprocessor to have the controller give control to a critical error handler at operation 516, which then performs its responsibilities to stop the functionality in a safe state and engage the audible alarm.

If there is no activity of the SMBus, at operation 510, then at operation 518, the microprocessor can check a voltage divider for the tethered cable for a proper voltage signal threshold.

If there is no voltage at the tethered cable, at operation 520, then the software can direct the microprocessor to have the controller give control to the critical error handler at operation 522, which then performs its responsibilities to stop the functionality in a safe state and engage the audible alarm.

If there is a proper voltage signal threshold at the tethered cable, at operation 520, then at operation 524, the controller can perform the remainder of the startup sequence checks. If the startup checks pass (e.g., the controller does not find any components in a fault condition) at operation 526, then the startup is successful, at operation 528. If the startup checks do not pass (e.g., the controller finds at least one component in a fault condition) at operation 526, then then the software can direct the microprocessor to have the controller give control to the critical error handler at operation 522, which then performs its responsibilities to stop the functionality in a safe state and engage the audible alarm.

The critical error handler can be called at any point to take control of an unstable system, optionally including during start-up of the controller if needed.

FIG. 6 shows a flowchart of an example of a method 600 for executing a critical error handler 412 for a surgical power tool, in accordance with some embodiments. FIG. 6 provides a detailed augmentation of operations 406, 408, and 410 from FIG. 4, in which the controller executes a critical error handler. Method 600 is but one method for executing a critical error handler; other suitable methods can also be used.

At operation 602, the controller can invoke the critical error handler.

At operation 604, the critical error handler can disable all software tasks.

At operation 606, the critical error handler can disable the voltage that drives the electric motor.

At operation 608, the critical error handler can disable the function of the trigger.

At operation 610, the critical error handler can disable the mode switch.

At operation 612, the critical error handler can engage an audible alarm, such as a beep.

At operation 614, the critical error handler can log the error (e.g., which component or components were in a fault condition) in memory.

At operation 616, the critical error handler can send the software into an infinite loop. Operations 604-616 can be executed in any suitable order.

At operation 618, the critical error handler can wait for removal of power, to overcome the infinite loop.

FIG. 7 shows a flowchart of an example of a method 700 for executing a start-up integrity check for a surgical power tool, in accordance with some embodiments. The start-up integrity check can be executed by a controller of a surgical power tool, such as controller 108 (FIG. 1). The method 700 is but one example of a method for executing a start-up integrity check for a surgical power tool; other suitable methods can also be used.

At operation 702, the controller can receive a request to perform a start-up check.

At operation 704, the controller can send all previously stored errors to the serial port of the controller. In some examples, the controller can send the serial data to an external computer through a USB port. In other cases, the controller can send the serial data to the external computer wirelessly.

At operation 706, the controller can interrogate to determine a power source.

At operation 708, the controller can query whether a battery is attached. If no battery is detected, the controller can query whether a power cable is attached, at operation 714. If a battery is detected at operation 708, then at operation 710, the controller can check the authenticity of the battery.

At operation 712, the controller can check a value of the primary direct current (DC) power presented by a primary DC regulator. In some example, this check can also include lower level logic supplies, such as at operation 716 (first logic power supply) and operation 718 (second logical power supply).

At operation 720, the controller can perform memory tests to ensure that memory is reading and writing properly.

At operation 722, the controller can ensure that software has the proper cyclic redundancy check (CRC) calculation.

At operation 724, the controller can test the serial electrically erasable programmable read-only memory (EEPROM) to ensure that the controller can properly read and write to the serial EEPROM.

At operation 726, the controller can check the Hall effect sensors in the electric motor.

At operation 728, the controller can check the phases in the electric motor.

At operation 730, the controller can check the temperature of the electronics, including the controller.

At operation 732, the controller can check the temperature of the electric motor and/or the motor case.

At operation 734, the controller can check Hall effect sensors for the trigger. The trigger Hall effect sensors can determine how far each trigger button is depressed.

At operation 736, the controller can check a trigger status to ensure that the trigger is not showing input that would cause the system to run upon connecting power.

At operation 738, the controller can check a mode switch Hall effect sensor. The mode switch Hall effect sensor can determine the setting at which the mode switch is set.

At operation 740, the controller can check for watchdog timer errors that are internal to the microprocessor in the controller.

At operation 742, the controller can check the battery for proper health as reported by the battery pack's battery management system. Operations 704-742 can be execute in any suitable order.

If, at operation 744, the controller deems that one or more checks are unsuccessful (e.g., at least one component is found to be in a fault condition), the controller activates the critical error handler at operation 748. An example of a suitable critical error handler is described above and shown in FIG. 6.

If, at operation 744, the controller deems that all the checks are passed successfully, the controller can turn on functionality of the surgical power tool, at operation 746. After operation 746, the surgical power tool can be used normally. Following operation 746, the controller can execute self-monitoring checks at specified times while the surgical power tool is powered up. In some examples, the self-monitoring checks can occur at periodic (e.g., evenly spaced) intervals. In other examples, the intervals may not be evenly spaced.

FIG. 8 shows a flowchart of an example of a method 800 for executing a self-monitoring check for a surgical power tool, in accordance with some embodiments. FIG. 8 provides a detailed example of operation 402 from FIG. 4, in which the controller interrogates the plurality of components. The method 800 can be executed by a controller of a surgical power tool. This is but one example of a method for executing a self-monitoring check for a surgical power tool; other suitable methods can also be used.

At operation 802, the controller can receive a request to initiate a self-monitoring check (e.g., a request to interrogate various components in the surgical power tool to look for faults). In some examples, one module in the controller can receive the request from another module in the controller. In other examples, the controller can receive the request from a component external to the controller.

At operation 804, the controller can check the bulk power supply when not under load (e.g., when the electric motor is idle).

At operation 806, the controller can check the bulk power supply under a load (e.g., when the electric motor is running).

At operation 808, the controller can check a first logic power supply.

At operation 810, the controller can check a second logic power supply. If the surgical power tool includes addition logic power supplies, the controller can check those as well.

At operation 812, the controller can check Hall sensors in the electric motor.

At operation 814, the controller can check phases in the electric motor.

At operation 816, the controller can check a temperature of the electronics, which can include the controller.

At operation 818, the controller can check a temperature of the motor case, which can include the electric motor.

At operation 820, the controller can check Hall effect sensors for the trigger, which can include the trigger button or buttons.

At operation 822, the controller can check one or more Hall effect sensors in the mode switch.

At operation 824, the controller can check for errors in a watchdog timer that is internal to the microprocessor in the controller.

At operation 826, the controller can check for any unexpected software interrupts that can undesirably occur within the microprocessor of the controller.

At operation 828, the controller can check for any EEPROM write errors so that any new failure mode can be properly logged.

At operation 830, the controller can check for any illegal data values and/or illegal program executions that may have occurred in the microprocessor of the controller.

At operation 832, the controller can check a current at the bulk power supply, a current in the electric motor phases, and a voltage in the electric motor phases to ensure that the bulk power supply and electric motor are not overloaded.

At operation 834, the controller can check if there are any faults reported by the battery.

At operation 836, the controller can ensure that the battery is communicating properly. Operations 804-836 can be executed in any suitable order.

At operation 838, the controller can determine if all the checks pass, or at least one check fails. If at least one check fails, the controller can invoke the critical error handler at operation 842, such as outlined in FIG. 6. If all the checks pass, the controller can continue functionality of the surgical power tool at operation 840.

To further illustrate the device and related method disclosed herein, a non-limiting list of examples is provided below. Each of the following non-limiting examples can stand on its own, or can be combined in any permutation or combination with any one or more of the other examples.

In Example 1, a surgical power tool can include: a housing; an electric motor positioned in the housing; a movable element extending from the housing and operatively actuated by the electric motor; and a controller positioned in the housing and configured to: repeatedly interrogate a plurality of components in or on the housing to determine if any of the plurality of components are in a fault condition, the plurality of components including the electric motor; and when at least one of the plurality of components is in a fault condition, engage a critical error handler that: disengages the electric motor, disables at least some of the plurality of components, and directs a microprocessor in the controller into a safe software state.

In Example 2, the surgical power tool of Example 1 can optionally be configured such that the controller is configured to repeatedly interrogate the electric motor for at least one of voltage, current, temperature, and phase elements.

In Example 3, the surgical power tool of any one or a combination of Examples 1-2 can optionally be configured such that the plurality of components includes a motor temperature sensor configured to measure a temperature of the electric motor; and the controller is configured to determine that the electric motor is in the fault condition when the measured temperature of the electric motor exceeds a stored motor temperature value.

In Example 4, the surgical power tool of any one or a combination of Examples 1-3 can optionally be configured such that the plurality of components includes a plurality of motor Hall effect sensors configured to determine a phase of the electric motor and generate a signal representing a speed of the electric motor when the electric motor is operational; and the controller is configured to determine that the plurality of motor Hall effect sensors are in the fault condition when at least one of the plurality of motor Hall effect sensors produces a voltage outside a specified motor Hall effect sensor voltage range.

In Example 5, the surgical power tool of any one or a combination of Examples 1-4 can optionally be configured such that: the plurality of components includes a battery configured to supply electrical power to the controller; the controller is configured to repeatedly interrogate the battery for at least one of a system voltage, a battery pack status flag, and a temperature; and the controller is configured to determine that the battery is in the fault condition when at least one of the system voltage, battery pack status flag, or temperature exceeds a respective stored value.

In Example 6, the surgical power tool of any one or a combination of Examples 1-5 can optionally be configured such that: the plurality of components includes a trigger coupled to the controller and configured to turn on the electric motor when the trigger is depressed and adjust a speed of the electric motor based on how far the trigger is depressed; the plurality of components includes a plurality of trigger Hall effect sensors configured to generate a signal representing a position of the trigger; the controller is configured to determine that the plurality of trigger Hall effect sensors are in the fault condition when at least one of the plurality of trigger Hall effect sensors produces a voltage outside a specified trigger Hall effect sensor voltage range; and the controller is configured to disable the trigger when at least one of the plurality of components is in a fault condition.

In Example 7, the surgical power tool of any one or a combination of Examples 1-6 can optionally be configured such that: the plurality of components includes a mode switch coupled to the controller and configured to select among at least two specified modes of operation for the controller; the plurality of components includes a plurality of mode Hall effect sensors configured to generate a signal representing a position of the mode switch; the controller is configured to determine that the plurality of mode Hall effect sensors are in the fault condition when the at least one of the plurality of mode Hall effect sensors produces a voltage outside a specified mode Hall effect sensor voltage range; and the controller is configured to disable the mode switch when at least one of the plurality of components is in a fault condition.

In Example 8, the surgical power tool of any one or a combination of Examples 1-7 can optionally be configured such that: the plurality of components includes a controller temperature sensor configured to measure a temperature of the controller; and the controller is configured to determine that the controller is in the fault condition when the measured temperature of the controller exceeds a stored controller temperature value.

In Example 9, the surgical power tool of any one or a combination of Examples 1-8 can optionally be configured such that: the controller is configured to repeatedly interrogate at least one of a first logic power supply, a second logic power supply, a watchdog timer, an unexpected software interrupt, a serial electrically erasable programmable read-only memory write error, an illegal data value, and an illegal program execution; and the controller is configured to determine that the controller is in the fault condition when the controller finds fault with at least one of the first logic power supply, second logic power supply, watchdog timer, unexpected software interrupt, serial electrically erasable programmable read-only memory write error, illegal data value, or illegal program execution.

In Example 10, the surgical power tool of any one or a combination of Examples 1-9 can optionally be configured to further include a sound emitter coupled to the controller, wherein the critical error handler causes the sound emitter to emit an audible alarm.

In Example 11, the surgical power tool of any one or a combination of Examples 1-10 can optionally be configured such that the interrogating is performed periodically with an interrogation frequency.

In Example 12, the surgical power tool of any one or a combination of Examples 1-11 can optionally be configured such that the controller is further configured to, after the controller has been powered up and before the electric motor is engaged: interrogate the plurality of components to determine if any of the plurality of components are in a fault condition; and when at least one of the plurality of components is in a fault condition, engage the critical error handler.

In Example 13, the surgical power tool of any one or a combination of Examples 1-12 can optionally be configured such that the controller is further configured to, upon engaging the critical error handler, write to a serial electrically erasable programmable read-only memory an error code corresponding to which of the plurality of components is in the fault condition; and the error code is accessible via a wired or wireless connection.

In Example 14, a method for monitoring the operation of a surgical power tool, the surgical power tool can include a plurality of components positioned in or on a housing, the method comprising: with the controller, periodically interrogating the plurality of components to determine if any of the plurality of components are in a fault condition; and when at least one of the plurality of components is in a fault condition, engaging a critical error handler that: disengages an electric motor, disables at least some of the plurality of components, and directs a microprocessor in the controller into a safe software state.

In Example 15, the method of Example 14 can optionally further comprise: wherein: the plurality of components includes the electric motor, a controller coupled to the electric motor, a battery configured to supply electrical power to the controller, a trigger coupled to the controller and configured to turn on the electric motor when the trigger is depressed and adjust a speed of the electric motor based on how far the trigger is depressed, and a mode switch coupled to the controller and configured to select among at least two specified modes of operation for the controller; and the critical error handler disables the trigger and the mode switch.

In Example 16, the method of any one or a combination of Examples 14-15 can optionally be configured such that the critical error handler further writes to a serial electrically erasable programmable read-only memory an error code corresponding to which of the plurality of components is in the fault condition, the error code being accessible via a wired or wireless connection In Example 17, a surgical power tool can include a housing; an electric motor positioned in the housing; a movable element extending from the housing and operatively actuated by the electric motor; a controller positioned in the housing; a battery configured to supply electrical power to the controller; a trigger coupled to the controller and configured to turn on the electric motor when the trigger is depressed and adjust a speed of the electric motor based on how far the trigger is depressed; and a mode switch coupled to the controller and configured to select among at least two specified modes of operation for the controller, wherein the electric motor, the controller, the battery, the trigger, and the mode switch form a plurality of components; and wherein the controller is configured to: repeatedly interrogate the plurality of components to determine if any of the plurality of components are in a fault condition; and when at least one of the plurality of components is in a fault condition, engage a critical error handler that: disengages the electric motor, disables the trigger and the mode switch, directs a microprocessor in the controller into a safe software state, and causes a sound emitter to emit an audible alarm.

In Example 18, the surgical power tool of Example 17 can optionally be configured such that the interrogating is performed periodically with an interrogation frequency.

In Example 19, the surgical power tool of any one or a combination of Examples 17-18 can optionally be configured such that the controller is further configured to, after the controller has been powered up and before the electric motor is engaged: interrogate the plurality of components to determine if any of the plurality of components are in a fault condition; and when at least one of the plurality of components is in a fault condition, engage the critical error handler.

In Example 20, the surgical power tool of any one or a combination of Examples 17-19 can optionally be configured such that the controller is further configured to, upon engaging the critical error handler, write to a serial electrically erasable programmable read-only memory an error code corresponding to which of the plurality of components is in the fault condition; and the error code is accessible via a wired or wireless connection.

While this invention has been described as having example designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical power tool, comprising:
   a housing;
   an electric motor positioned in the housing;
   a movable element extending from the housing and operatively actuated by the electric motor; and
   a controller positioned in the housing and configured to:
      repeatedly interrogate a plurality of components in or on the housing to determine if any of the plurality of components are in a fault condition, the plurality of components including the electric motor; and
      when at least one of the plurality of components is in a fault condition, engage a critical error handler that:
         disengages the electric motor,
         disables at least some of the plurality of components, and
         directs a microprocessor in the controller into a safe software state.

2. The surgical power tool of claim 1, wherein the controller is configured to repeatedly interrogate the electric motor for at least one of voltage, current, temperature, and phase elements.

3. The surgical power tool of claim 1, wherein:
   the plurality of components includes a motor temperature sensor configured to measure a temperature of the electric motor; and
   the controller is configured to determine that the electric motor is in the fault condition when the measured temperature of the electric motor exceeds a stored motor temperature value.

4. The surgical power tool of claim 1, wherein:
   the plurality of components includes a plurality of motor Hall effect sensors configured to determine a phase of the electric motor and generate a signal representing a speed of the electric motor when the electric motor is operational; and
   the controller is configured to determine that the plurality of motor Hall effect sensors are in the fault condition when at least one of the plurality of motor Hall effect sensors produces a voltage outside a specified motor Hall effect sensor voltage range.

5. The surgical power tool of claim 1, wherein:
   the plurality of components includes a battery configured to supply electrical power to the controller;
   the controller is configured to repeatedly interrogate the battery for at least one of a system voltage, a battery pack status flag, and a temperature; and
   the controller is configured to determine that the battery is in the fault condition when at least one of the system voltage, battery pack status flag, or temperature exceeds a respective stored value.

6. The surgical power tool of claim 1, wherein:
   the plurality of components includes a trigger coupled to the controller and configured to turn on the electric motor when the trigger is depressed and adjust a speed of the electric motor based on how far the trigger is depressed;
   the plurality of components includes a plurality of trigger Hall effect sensors configured to generate a signal representing a position of the trigger;
   the controller is configured to determine that the plurality of trigger Hall effect sensors are in the fault condition when at least one of the plurality of trigger Hall effect sensors produces a voltage outside a specified trigger Hall effect sensor voltage range; and
   the controller is configured to disable the trigger when at least one of the plurality of components is in a fault condition.

7. The surgical power tool of claim 1, wherein:
   the plurality of components includes a mode switch coupled to the controller and configured to select among at least two specified modes of operation for the controller;
   the plurality of components includes a plurality of mode Hall effect sensors configured to generate a signal representing a position of the mode switch;
   the controller is configured to determine that the plurality of mode Hall effect sensors are in the fault condition when the at least one of the plurality of mode Hall effect sensors produces a voltage outside a specified mode Hall effect sensor voltage range; and
   the controller is configured to disable the mode switch when at least one of the plurality of components is in a fault condition.

8. The surgical power tool of claim 1, wherein:
   the plurality of components includes a controller temperature sensor configured to measure a temperature of the controller; and
   the controller is configured to determine that the controller is in the fault condition when the measured temperature of the controller exceeds a stored controller temperature value.

9. The surgical power tool of claim 1, wherein:
   the controller is configured to repeatedly interrogate at least one of a first logic power supply, a second logic power supply, a watchdog timer, an unexpected software interrupt, a serial electrically erasable programmable read-only memory write error, an illegal data value, and an illegal program execution; and
   the controller is configured to determine that the controller is in the fault condition when the controller finds fault with at least one of the first logic power supply, second logic power supply, watchdog timer, unexpected software interrupt, serial electrically erasable programmable read-only memory write error, illegal data value, or illegal program execution.

10. The surgical power tool of claim 1, further comprising a sound emitter coupled to the controller, wherein the critical error handler causes the sound emitter to emit an audible alarm.

11. The surgical power tool of claim 1, wherein the interrogating is performed periodically with an interrogation frequency.

12. The surgical power tool of claim 1, wherein the controller is further configured to, after the controller has been powered up and before the electric motor is engaged:
   interrogate the plurality of components to determine if any of the plurality of components are in a fault condition; and
   when at least one of the plurality of components is in a fault condition, engage the critical error handler.

13. The surgical power tool of claim 1, wherein:
   the controller is further configured to, upon engaging the critical error handler, write to a serial electrically erasable programmable read-only memory an error code corresponding to which of the plurality of components is in the fault condition; and the error code is accessible via a wired or wireless connection.

14. A method for monitoring the operation of a surgical power tool, the surgical power tool including a plurality of components positioned in or on a housing, the method comprising:
    with the controller, periodically interrogating the plurality of components to determine if any of the plurality of components are in a fault condition; and
    when at least one of the plurality of components is in a fault condition, engaging a critical error handler that:
        disengages an electric motor,
        disables at least some of the plurality of components, and
        directs a microprocessor in the controller into a safe software state.

15. The method of claim 14, wherein:
    the plurality of components includes the electric motor, a controller coupled to the electric motor, a battery configured to supply electrical power to the controller, a trigger coupled to the controller and configured to turn on the electric motor when the trigger is depressed and adjust a speed of the electric motor based on how far the trigger is depressed, and a mode switch coupled to the controller and configured to select among at least two specified modes of operation for the controller; and
    the critical error handler disables the trigger and the mode switch.

16. The method of claim 14, wherein the critical error handler further writes to a serial electrically erasable programmable read-only memory an error code corresponding to which of the plurality of components is in the fault condition, the error code being accessible via a wired or wireless connection.

17. A surgical power tool, comprising:
    a housing;
    an electric motor positioned in the housing;
    a movable element extending from the housing and operatively actuated by the electric motor;
    a controller positioned in the housing;
    a battery configured to supply electrical power to the controller;
    a trigger coupled to the controller and configured to turn on the electric motor when the trigger is depressed and adjust a speed of the electric motor based on how far the trigger is depressed; and
    a mode switch coupled to the controller and configured to select among at least two specified modes of operation for the controller,
    wherein the electric motor, the controller, the battery, the trigger, and the mode switch form a plurality of components; and
    wherein the controller is configured to:
        repeatedly interrogate the plurality of components to determine if any of the plurality of components are in a fault condition; and
        when at least one of the plurality of components is in a fault condition, engage a critical error handler that:
            disengages the electric motor,
            disables the trigger and the mode switch,
            directs a microprocessor in the controller into a safe software state, and
            causes a sound emitter to emit an audible alarm.

18. The surgical power tool of claim 17, wherein the interrogating is performed periodically with an interrogation frequency.

19. The surgical power tool of claim 17, wherein the controller is further configured to, after the controller has been powered up and before the electric motor is engaged:
    interrogate the plurality of components to determine if any of the plurality of components are in a fault condition; and
    when at least one of the plurality of components is in a fault condition, engage the critical error handler.

20. The surgical power tool of claim 17, wherein:
    the controller is further configured to, upon engaging the critical error handler, write to a serial electrically erasable programmable read-only memory an error code corresponding to which of the plurality of components is in the fault condition; and
    the error code is accessible via a wired or wireless connection.

* * * * *